(12) United States Patent
Iftner

(10) Patent No.: US 6,902,899 B2
(45) Date of Patent: Jun. 7, 2005

(54) DETECTION OF HUMAN PAPILLOMAVIRUSES

(75) Inventor: Thomas Iftner, Hirrlingen (DE)

(73) Assignee: Eberhard-Karls-Universitat Tubingen Universitatsklinikum, Tubingen (DE)

( * ) Notice: Subject to any disclaimer, the term of this patent is extended or adjusted under 35 U.S.C. 154(b) by 385 days.

(21) Appl. No.: 10/227,638

(22) Filed: Aug. 22, 2002

(65) Prior Publication Data

US 2003/0129585 A1 Jul. 10, 2003

Related U.S. Application Data

(63) Continuation of application No. PCT/EP01/02003, filed on Feb. 22, 2001, now abandoned.

(30) Foreign Application Priority Data

Feb. 26, 2000 (DE) .......................................... 100 09 143

(51) Int. Cl.[7] .............................. C12Q 1/70; C12P 19/34
(52) U.S. Cl. ........................... 435/6; 435/91.2; 435/91.1
(58) Field of Search .................. 435/6, 91.2; 536/24.3, 536/24.32

(56) References Cited

FOREIGN PATENT DOCUMENTS

| DE | 19530332 C2 | 8/1995 |
|----|-------------|--------|
| DE | 19530333 C2 | 8/1995 |
| DE | 19530336 C2 | 8/1995 |
| DE | 19535347 C1 | 8/1996 |
| EP | 0425995 | 5/1991 |
| WO | WO 00/50645 | 8/2000 |

OTHER PUBLICATIONS

GenBank Accession X74477, GI: 396997, Feb. 24, 19999, Human papillomavirus type 35H genomic DNA.*

Cole, S.T. and Streeck, R. E. (1987) Genome organization and nucleotide sequence of human papillomavirus type 33, which is associated with cervical cancer. Database EMBL Accession M12732.

Egawa, K., et al. (1993) Two noevel types of human papillomavirus, HPV63 and HPV65: comparisons of their distinct clinical and hitological features and their DNA sequences to other HPV types. Database EMBL Accession X70827.

Goldsborough, M. D., et al. (1989) Nucleotide sequence of human papillomavirus type 31: A cervical neoplasia associated virus. Database EMBL Accession J04353.

Tieben, L. M., et al. (1993) Detection of cutaneous and genital HPV types in clinical samples by PCR using consensus primers. J. Virol. Meth. 42:265–280.

Ylitalo, N., et al. (1995) Detection of Genital Human Papillomavirus by Single–Tube Nested PCR and Type–Specific Oligonucleotide–Hybridization. J. Clin. Microbiol. 33(7):1822–1828.

Dean, David et al., "Fungal Infection in Surgical Patients," American Journal of Surgery, vol. 171, pp. 374–382 (1996).

Einsele, Hermann et al., "Detection and Identification of Fungal Pathogens in Blood by Using Molecular Probes," Journal of Clinical Microbiology, vol. 35, No. 6, pp. 1353–1360 (1997).

Van Burik, Joanne et al., "Panfungal PCR Assay for Detection of Fungal Infection in Human Blood Specimens," Journal of Clinical Microbiology, vol. 36, No. 5, pp. 1169–1175 (1998).

Wenzel, Richard P., "Nosocomial Candidemia: Risk Factors and Attributable Mortality." Clinical Infectious Diseases, vol. 20, pp. 1531–1534 (1995).

* cited by examiner

Primary Examiner—Juliet C. Switzer
(74) Attorney, Agent, or Firm—Knobbe, Martens, Olson & Bear, LLP

(57) ABSTRACT

A method for detecting human papillomaviruses (HPV) in biological material is described, in which method nucleic acids are extracted/isolated from biological material and HPV-specific DNA is detected in the isolated nucleic acids. This method uses at least one of the nucleotide sequences SEQ ID No. 1 or SEQ ID No. 2 from the enclosed sequence listing or sequences which bind to sequences to which one of the sequences SEQ ID No. 1 or SEQ ID No. 2 binds or sequences which are complementary to the abovementioned sequences.

10 Claims, 1 Drawing Sheet

DETECTION OF HUMAN PAPILLOMAVIRUSES

RELATED APPLICATION

This is a continuation application of International Patent Application PCT/EP01/02003, in which the United States is a designated country, with an international filing date of Feb. 22, 2001, published in German under PCT Article 21(2) and now abandoned, which claims priority to a German Application 10009143.1 filed Feb. 26, 2000.

BACKGROUND OF THE INVENTION

1. Field of the Invention

The present invention relates to a method for detecting human papillomaviruses (HPV) in biological material and to nucleotide sequences which are used in the method.

This method comprises the steps of:.
a) extracting/isolating nucleic acids from biological material, and
b) detecting HPV-specific DNA in the isolated nucleic acids.

2. Related Prior Art

Various publications have disclosed a method of this nature.

Infections with HPV are connected with a large number of diseases of the skin and the mucous membrane. These diseases are usually benign tumors which appear as condylomas, warts or papillomas which as a rule heal spontaneously after a period lasting from months to years. With the aid of molecular biology and genetic manipulation it has also been possible to demonstrate the connection which exists between a variety of cancers and infections with papillomavirus. These tumors are, in particular, carcinomas of the anogenital region, i.e. particularly carcinomas of the uterine cervix but also skin carcinomas in the case of immunosuppressed patients or patients suffering from the rare disease of epidermodysplasia verruciformis (EV). It has by now become generally accepted that HPV is causally involved in the cancers in the region of the anogenital tract. All over the world, HPV DNA is detected in virtually all uterine cervical carcinomas and precursor lesions.

More than 100 HPV genotypes have by now been identified, with the clinical syndromes which can be caused by the infection frequently being characteristic of a particular HPV type. Vulgar warts of the limbs and plantar warts are caused, in particular, by HPV types 1, 2, 4, 10, 27, 28, 57 and 65. In accordance with their oncogenic potential, the EPVs which are connected with cancers in the anogenital region are subdivided into "low-risk" (e.g. 6, 11 and 40) and "high-risk" HPV types (e.g. 16, 18, 45 and 56). Low-risk HPV types principally cause benign tumors of the external genital region (condylomas) and low-grade intraepithelial neoplasias and are only rarely associated with carcinomas. On the other hand, the presence of high-risk viruses in epithelial cells of the anogenital tract constitutes a high risk factor for the development of a carcinoma. HPV types 5 and 8 are regarded as being to a large extent certain to be involved in the development of skin carcinomas in EV patients.

Cancer of the uterine cervix and certain forms of skin cancer are avoidable diseases if early diagnosis and treatment are ensured. A method which reliably detects the presence of an HPV infection, which encompasses all the HPV types and which, in addition to this, enables the virus to be typed, is therefore a prerequisite for selective therapy.

Histological methods (cytology screening) have been used since the 1950s for detecting precancerous lesions and precociously invasive carcinomas. The use of these methods resulted in a decline in the incidents of cervical cancer. Despite this, the cytology is methodologically inadequate, thereby leading both to falsely negative (invasive carcinomas 15% to 55%, precociously invasive carcinomas 20% to 70%) and falsely positive results (5% to 15%, thereby causing unnecessary anxiety to the patients). These inadequacies are:

Subjective errors—the cytology is complex; it requires intensive visual examination of cells. This technique is not objective, nor is it geographically standardized.

Erroneous or faulty sample isolation can lead to falsely negative or unclear results.

Histological methods generally only record the existing state of a tissue, which means that these methods lack prognostic value.

As a result of the detection methods having been improved, it has by now become possible to detect the presence of papilloma-virus directly in infected tissues:

The method termed HCM (hybrid capture microplate), which is a test which can be obtained commercially from Digene Corp., Gaithersburg, Md., USA, is a signal-amplifying hybridization method. This method makes it possible to qualitatively detect 18 HPV types in uterine cervix tissue samples. The hybridization probes which are used are HPV-specific RNA sequences which cover the entire viral genome.

Incubating these probes with denatured HPV DNA from the infected tissue results in the formation of RNA/DNA hybrids, which can be detected using a specific antibody. The enzyme alkaline phosphatase, which is conjugated to the antibody, is used to detect the virus by means of chemiluninescence, after an appropriate substrate has been added.

The HCM method makes it possible to differentiate between two HPV DNA groups: HPV types 6, 11, 42, 43 and 44, which have a low carcinogenic potential, and HPV types 16, 18, 31, 33, 35, 39, 45, 51, 52, 56, 58, 59 and 68, which have a medium to high carcinogenic potential.

It is not possible to use, this method to type the papillomaviruses precisely. A disadvantage of this test method is, furthermore, that the use of an RNA mixture frequently results in cross reactions taking place between the two HPV classes. This can lead to falsely negative or falsely positive results. Another disadvantage is that this method does not detect the HPV 5 and 8 papillomaviruses.

Surentheran et al., "Detection and typing of Human Papilloma Viruses in mucosal and cutaneous biopsy from immunosuppressed and immunocompetent patients and patients with Epidermodysplasia verruciformis: A unified diagnostic approach", Journal of Clinical Pathology 1998; 51:606–610, describe a polymerase chain reaction (PCR)-based method for detecting HPV DNA in skin biopsies and mucous membrane biopsies from immunosuppressed patients, from immunocompetent patients and from EV patients. For this, the authors use a variety of PCR primer pairs which all lie within the open reading frame of the viral gene encoding the structural protein L1.

The papillomaviruses are typed by subsequently analyzing the sequence of the amplified gene fragment. Recent investigations have shown that the L1 gene is less conserved, over all the known HPV types, than was originally assumed. For this reason, this method only succeeds in detecting a limited number of HPV types (HPV 2–6, 8, 10, 11, 16, 31, 41 and 57). There has been no report on whether is it possible to use this method to detect the high-risk HPV types 18, 45 and 56.

Jacobs et al., "Group-Specific Differentiation between High- and Low-Risk Human Papillomavirus Genotypes by General Primer-Mediated PCR and Two Cocktails of Oligonucleotide Probes", Journal of Clinical Microbiology 1995, 33, 901–905, also use a primer pair, designated GP5+/GP6+, which lies within the viral gene encoding the L1 structural protein. The region of the L1 gene which is amplified in the PCR using this primer pair is 150 base pairs (bp) in length. Following gel-electrophoretic fractionation, specific probes can be used to assign the amplificates to the high-risk HPV types 16, 18, 31, 33, 35, 39, 45, 51, 52, 54, 56 and 58 and to the low-risk HPV types 6, 11, 34, 40, 42, 43 and 44. The specific hybridization probes are in each case 30 bases in length.

Tieben et al., "Detection of Epidermodysplasia verruciformis-like human papillomavirus types in malignant and premalignant skin lesions of renal transplant recipients", British Journal of Dermatology 1994; 131, 226–230, describe a method for detecting HPV DNA in skin tumors of patients following a kidney transplant, which method is likewise PCR-based. The various PCR primer pairs which are used in this instance lie within the conserved, virus-specific E1 gene, which encodes an ATP-dependent DNA helicase. By means of using four different PCR primer pairs, the authors succeed in detecting the following HPV types: HPV 1–5, 6b, 7–9, 10a, 11, 12, 14a, 15, 16–22, 24, 25, 31, 33, 36–38, 46, 49, 50 and 65. However, the inventor of the present application has found that the primer pair CP4/CP5 is not suitable for amplification.

In this publication, typing is effected by sequencing the amplificate. In this connection, it is noteworthy that only three of the abovementioned primer pairs can be used if the PCR is to be followed by a typing of this nature. The abovementioned primer pair CP4/CP5 cannot be used. Using this method, Tieben et al. succeed, by typing, in specifically detecting the HPV types 1a, 2a, 3–5, 6b, 8, 10a, 11–13, 14a, 15–18, 20–22, 24, 25, 31, 33, 36, 39, 41, 42, 46, 47, 49, 50, 57, 58, 63 and 65.

The advantage as compared with the method described by Surentheran et al. is that, in this present method, a larger number of different HPV types can be identified with one primer pair. Despite this improvement in the specificity, it is not possible to use this method to type a large number of HPVs, in particular the high-risk papillomaviruses HPV 45 and 56 and also HPV types 35, 51 and 52, which have medium oncogenic potential.

However, as far as the inventor of the present application is aware, the primer pair CP4/CP5 is not used routinely in hospitals; on the contrary, hospitals are currently only using primer pairs which lie within the L1 gene, such as the primer pair GP5+/GP6+ described by Jacob et al., loc. cit.

SUMMARY OF THE INVENTION

In view of the above, it is an object of the present invention to provide a method of the type mentioned at the outset, which method makes it possible to reliably detect all the HPV viruses which currently come into consideration in connection with tumor induction, and also to provide hybridization sequences for this method.

In the method mentioned at the outset, this object is achieved, according to the invention, by the detection being effected by way of specific HPV DNA segments using at least one of the following nucleotide sequences: SEQ ID No. 1, SEQ ID No. 2 or SEQ ID No. 3 from the enclosed sequence listing or sequences which bind (hybridize) to sequences to which at least one of the sequences SEQ ID No. 1, SEQ ID No. 2 or SEQ ID No. 3 bind(s) or sequences which are complementary to the abovementioned sequences.

The object underlying the invention is achieved completely in this manner. Thus, the inventor of the present application has found that, because of their high degree of specificity and sensitivity, it is possible to use the nucleotide sequences SEQ ID Nos. 1, 2 and 3, which are described here for the first time, to successfully detect all previously known HPV types. All three sequences are derived from the highly conserved viral E1 gene. The use of the sequences SEQ ID Nos. 1, 2 and 3, for example as hybridization probes (DNA markers) or in the context of a DNA amplification method, is therefore particularly suitable for detecting any HPV infection.

The described method leads to particularly good results when an HPV infection is detected by using a polymerase chain reaction (PCR) to amplify the specific HPV DNA segments.

The nucleotide sequences SEQ ID No. 1 and 2 are, for example, used as the PCR primer pair for this purpose. This results in the formation of an amplification product of approx. 220 bp in length, which product can be detected using simple standard methods, for example staining with ethidium bromide after fractionating by gel electrophoresis.

It is another object of the invention that the specific HPV DNA segments are amplified by means of a polymerase chain reaction (PCR) which is characterized by the following temperature profile:

| | |
|---|---|
| Heating: | 5–15 min., 90–100° C.; |
| Heat denaturation: | 30–90 sec., 90–100° C.; |
| Hybridization: | 30–90 sec., 50–60° C.; |
| Polymerization: | 30–180 sec., 67–77° C.; |
| Cooling: | 2–10 min., 67–77° C. |

The inventor of the present application has found that this temperature profile, which differs from other published profiles, is essential for an efficient amplification reaction and consequently for reliable typing. According to the inventor's findings, a particularly efficient PCR reaction is achieved under the following conditions:

| | |
|---|---|
| Heating: | 10 min., 95° C.; |
| Heat denaturation: | 30 sec., 95° C.; |
| Hybridization: | 30 sec., 55° C.; |
| Polymerization: | 1 min., 72° C.; |
| Cooling: | 5 min., 72° C.; |
| Heating rate: | 1° C./sec; |
| Cycles: | 40. |

Use of the sequence SEQ ID No. 1 together with sequence SEQ ID No. 3 as a PCR primer pair yields an amplification product of the viral E1 gene which is approx. 280 bp in length. Due to the length of the amplificate (as compared with the 220 bp amplificate when using SEQ ID No. 1 and SEQ ID No. 2 as the PCR primer pair) this makes it possible to type even more reliably, for example by means of a subsequent sequencing or temperature gradient gel electrophoresis, than is the case when using the SEQ ID Nos. 1 and 2 primer pair.

Another object is to be seen in the fact that the constitution of the nucleotide sequence SEQ ID No. 1, which is not degenerate at any position, facilitates any possible sequencing of the amplification product. By contrast, the primers used by Tieben et al. are degenerate in two and three positions, respectively. This results in very high quantities of primer having to be employed in the PCR and a greater number of problems arising in any sequencing which may subsequently be carried out.

Against this background, the invention has as a further object the use of the sequences SEQ ID Nos. 1 and 3 as a PCR primer pair in the described method.

It is also possible to use the described primer pairs in a quantitative PCR method which can be carried out on what is termed the LightCycler™ supplied by Roche Molecular Biochemicals. In this connection, the amplified DNA can be detected either using the dye CYBER™Green I, which is used for detecting double-stranded DNA, or else using sequence-specific DNA probes which are labeled with different dyes.

A particularly reliable typing of the HPVs is achieved by sequencing the amplified HPV DNA segments. Thus, the amplification product is namely characterized by small variations in sequence between the different HPV types, with these variations enabling a given type to be classified.

The described method is preferably employed as part of a method for diagnosis and/or early recognition, particularly in connection with cancers, for example uterine cervical cancer.

The inventor has found that this method, whose component parts have previously been used in other connections, predominantly in the research sphere, is a reliable diagnostic method in this regard.

The novel method is likewise suitable for being used within the context of an investigation aimed at the early diagnosis of cancers. Thus, it is only a confirmed positive finding with regard to an HPV infection which can be the starting point for a selective therapy.

The invention has as still a further object the nucleotide sequences SEQ ID Nos. 1, 2 and 3, which are used in the method and which are depicted in the enclosed sequence listing, and to nucleotide sequences which hybridize to the sequences to which the sequences SEQ ID No.1, SEQ ID No. 2 or SEQ ID No. 3 bind.

Thus, it is namely the case that while the nucleotide sequences according to the invention can be altered by truncation, extension, substitution, insertion and/or deletion, they are still functionally comparable. In the light of this, the invention also relates to nucleotide sequences which have been altered in this way.

The same applies to nucleotide sequences which are at least complementary to one of the abovementioned sequences.

Thus, the inventor has found that using complementary nucleotide sequences, which hybridize in a corresponding manner to the counterstrand of the HPV DNA, can lead to the same results in the above-described methods For this reason, such sequences are also part of the subject matter of the present invention.

One of the inventor's particular achievements lies in the finding that a nucleotide sequence from the HPV E1 open reading frame can be used for detecting, and even typing, HPV in the anogenital region, particularly in connection with a disease of the uterine cervix because, in all known HPV types, the E1 region exhibits a higher degree of conservation than does the L1 region.

The high degree of conservation of the viral E1 gene, as compared with that of the viral L1 gene, ensures that as many HPV types as possible are detected. Despite everything, minor variations in sequence which exist between the different HPV types also ensure reliable typing, contrary to expectation.

It will be understood that the abovementioned features can also be used individually or in a different combination from that specified without departing from the scope of the present invention.

The invention is explained below with the aid of examples, from which other features and advantages ensue.

DESCRIPTION OF PREFERRED EMBODIMENTS

EXAMPLE 1

DNA Extraction

Figure 1:
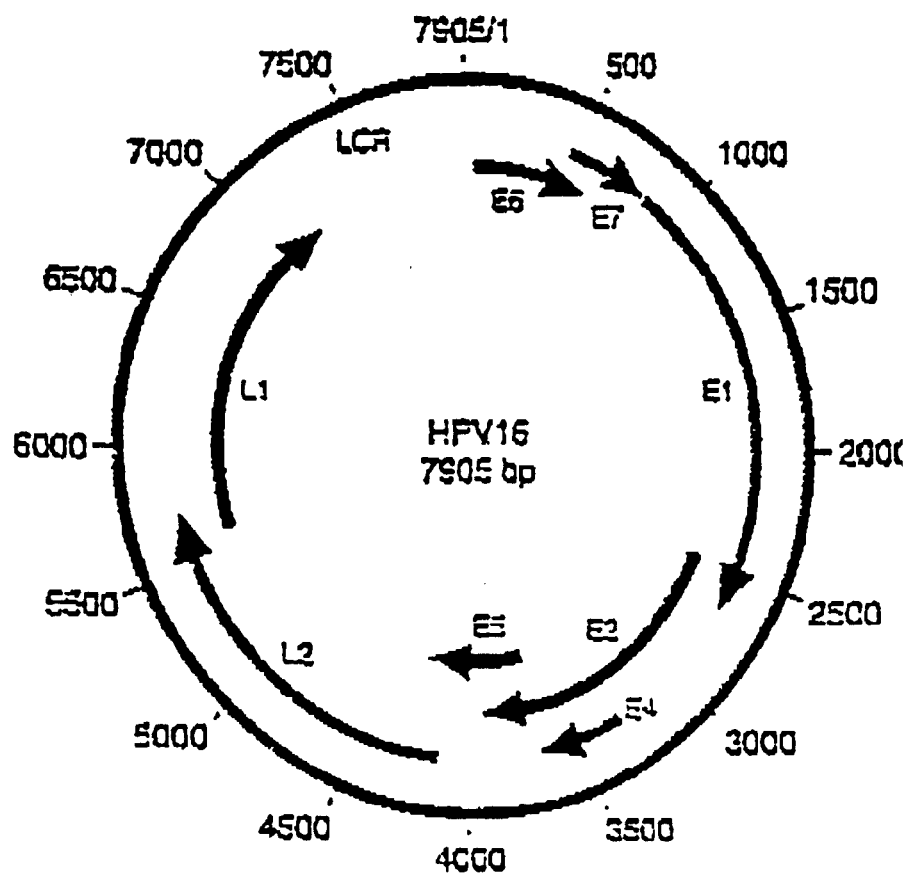
FIG. 1 shows the HPV16 genome.

For the purpose of detecting HPV, it is first of all necessary to remove biopsy or smear material. This is taken up in 500 µl of melting buffer (0.1 M EDTA; 0.05 M Tris, pH 8.0; 0.5% SDS). 2.5 µl of proteinase K (20 mg/ml) are then added to this and the solution is incubated at 55° C. for from 24 to 48 hours.

This is then followed by two extractions with phenol (phenol:CHCl$_3$:isoamyl alcohol=25.24:1). The preparation is mixed, not vortexed, incubated for 2–5 min. (rotated with inversion), and, after that, centrifuged at 14 000 rpm for 5 min. There then follows an extraction with CHCl$_3$/isoamyl alcohol (24:1) and incubation for 2–5 min and, after that, a centrifugation at 14 000 rpm for 5 min.

$^1$/$_{10}$ of the preparation volume of 7.5 M ammonium acetate is then added and the preparation is mixed and incubated at 55° C. for from 2 to 4 hrs.

The preparation is then precipitated with ethanol at −20° C. overnight.

The DNA which has been extracted in this way is subsequently used in a PCR reaction.

EXAMPLE 2

PCR Reaction

The PCR is used for selectively amplifying viral DNA segments.

0.25 µl, 1 µl, 2.5 µl and 5 µl of the extracted quantity of DNA are used for this purpose (without the concentration being determined); additions: primer 1: 100 ng, primer 2; 100 or 200 ng, dNTPs: in each case 10 mM; 5 µl of Taq polymerase buffer (10-fold, without MgCl$_2$); 7 µl of MgCl$_2$ (25 mM stock solution, corresponds to 3.6 mM); 0.4 µl of Taq Gold polymerase (corresponds to 2 units). The preparation is made up to a total volume of 50 µl. The PCR is performed in an MJ-Research Thermocycler (PTC 200); set heating rate: 1° C./sec. The PCR amplification takes place over 40 cycles [10 min. 95° C. (heating, only in the first cycle); 30 sec. 95° C.; 30 sec. 55° C.; 1 min. 72° C.; 5 min. 72° C. (cooling, only in the last cycle)].

For the purpose of nonspecifically detecting an HPV infection (screening), preference is given to using the sequences SEQ ID No. 1 (forward) and SEQ ID No. 2 (backward) as the primer pair (100 ng in each case). The nucleotide sequences of these primers, and their position in the HPV genome (HPV16 as an example) are:

SEQ ID No. 1
5'-(nt2082)-AAC-AAT-GTG-TAG-ACA-TTA-TAA-ACG-AGC-(nt2108)-3'

SEQ ID No. 2
5'-(nt2336)-ATT-AAA-CTC-ATT-CCA-AAA-TAT-GA-(nt2314)-3'

This screening method detects all the currently known HPV types.

If this is to be followed by a typing, for example by means of DNA sequencing, preference is then given to using the sequences SEQ ID No. 1 (forward) and SEQ ID No. 3 (backward; 200 ng) as the primer pair:

SEQ ID No. 3:
5'-(nt2401)-GAG-GYT-GCA-ACC-AAA-AMT-GRC-T-(nt2380)-3', where Y is a pyrimidine (T or C), M is amino (A or C) and R is a purine (G or A).

In the case of the backward primers SEQ ID Nos. 2 and 3, the positions which are given are those of the anticoding DNA strand, to which these primers are reverse and complementary.

EXAMPLE 3

DNA Sequencing (Typing)

The sequencing of the amplificate from Example 2, for the purpose of identifying the HPV type, is carried out using the ABI Big Dye Terminator Cycle Sequencing Ready Reaction Kit containing Ampli-Taq and using 200 ng of primer SEQ ID No. 1 or SEQ ID No. 3 and the PCR amplification preparation. This latter has previously been concentrated and purified through Microcon 100 columns (Millipore). Approx. 50% of the purified preparation is used for the sequencing.

The sequencing PCR reaction is carried out in accordance with the following conditions: 10 sec. 96° C., 5 sec. 55° C., 4 min. 60° C., 30 cycles, with a heating rate of 1° C./sec.

There then follows a precipitation with 0.3 M sodium acetate and 2.5 times the volume of ethanol.

The pellet is taken up in 25 µl of TSR (template suppression reagent from ABI), incubated at 90° C. for 2 min. and, after that, brought to 4° C. for 2 min. and subsequently kept at room temperature.

The capillary electrophoresis is carried out with the aid of the ABI prism 310 automated sequencing appliance and using a 47 cm capillary (diameter 50 µm), and is analyzed using the ABI 310 Genetic Analyser program. The polymer employed is the ABI Polymer POP 6 (performance optimized polymer 6).

When the primers SEQ ID No. 1 and SEQ ID. No. 3 are used, this typing can identify the following HPV types:

| | |
|---|---|
| HPV1 to HPV8 | HPV51 to HPV54 |
| HPV10 to HPV19 | HPV56 to HPV60 |
| HPV21 to HPV28 | HPV65 to HPV67 |
| HPV30 to HPV38 | HPV70 |
| HPV40 | HPV72 to HPV73 |
| HPV42 | HPV82 to HPV83 |
| HPV44 to HPV47 | |

Analogous results are obtained when the PCR primer pair SEQ ID No. 1 and SEQ ID No. 2 is used. Due to the smaller amplification product, it is not possible to differentiate between the following HPV types:

HPV51/HPV31
HPV31/HPV70
HPV18/HPV6
HPV18/HPV2a
HPV33/HPV1
HPV31/HPV83
HPV31/HPV57

EXAMPLE 4

Using a Nucleotide Sequence From the HPV E1 Open Reading Frame

In FIG. 1, the HPV genome is depicted, by way of examples by the HPV16 genome, which is 7 905 bp in length. The genome is divided into three sections: a non-coding region (LCR, long control region), an E (early) region, which encodes the "early genes", and an L (late) region, which encodes the "late genes", The position indicators show the position of the open reading frames.

According to the invention, one or more nucleotide sequences from the E1 open reading frame, which encodes an ATP-dependent DNA helicase, is/are used for detecting HPV such that all the HPV types are thereby detected. It is possible to use such sequences in the form of hybridization probes or also of PCR primers, etc. An HPV infection in the anogenital region, in particular in connection with a disease of the uterine cervix, comes particularly into consideration in this regard.

The E1 region is characterized by a high degree of conservation within the known HPV types. The E1 region is therefore particularly suitable for detecting any HPV infection. It has been found that, due to greater variations in the sequence between the different HPV types, falsely negative results can be obtained when the L1 open reading frame is used for detecting HPV. Using the E1 region minimizes this risk of erroneous detection.

However, the E1 region can also be used for typing the HPV; the inventor has found that the small differences in sequence are then, surprisingly, sufficient for this purpose.

EXAMPLE 5

Quantitative PCR Using the Primer Pair SEQ ID No. 1 and SEQ ID No. 3

The LightCycler™ is employed to detect the HPV33 genome using the primer pair SEQ ID No. 1 and SEQ ID No. 3. For this, tenfold LC-DNA Master Hybridization Fast-Start Probe-Mix (without $MgCl_2$) is used in accordance with the manufacturer's instructions and the final concentration of $MgCl_2$ is adjusted to 4 mM.

The quantity of HPV33 DNA employed was 30 ng, while the two primers were in each case used in a range from 0.45 to 0.9 µM.

The PCR amplification was carried out in accordance with the following protocol:

initial denaturation at 95° C., 10 minutes amplification (50 cycles) of in each case 95° C., 10 seconds, 55° C., 15 seconds and 72° C., 15 seconds. Cooling took place at 40° C. for 1 minute.

In all the steps but one, the heating rates were in each case 20° C./second; in the 72° C. step from the amplification, the rates were in each case 5° C./second.

The fluorescence was measured at the end of the annealing.

Using the dye CYBER™GREEN I, which binds to double-stranded DNA, it was possible to demonstrate, as compared with using an HPV plasmid standard, that this method had a sensitivity which still enabled only ten copies of HPV genome per sample to be detected.

Two sequence-specific DNA probes which were labeled with different dyes were used in another test. The sequences of the two probes are selected such that they are hybridized to the target sequence of the amplified DNA segment in such a way that the 3' end of one of the probes lies in close proximity to the 5' end of the other probe, with the two dyes being brought close to each other. One of the dyes is a donor dye and is excited by a short-wave-length light source, whereupon it emits fluorescent light at a somewhat longer wavelength. When the two dyes are located close to each other, the energy emitted by the donor dye excites the acceptor dye, which is located on the second hybridization probe and emits a fluorescent light at another wavelength.

The two following probes were used for detecting HPV33:

```
3' probe:   CGTAAAATGT CAATAGGACA ATGGATACAA

5' probe:   AGATGTGAAA AAACAAATGA TGGAGGAAA
```

The 3' probe was labeled with the dye LC-Red640 and the 5' probe was labeled with the dye FITC. Both the probes were used in a range from 0.15 to 0.25 μM.

The PCR amplification took place in accordance with the manufacturer's protocol; in this case, too, it was possible to demonstrate an achievable sensitivity of 10 genome copies per sample employed.

EXAMPLE 6

Comparison Between the Primer Pairs GP5+/GP6+ and SEQ ID No. 1/SEQ ID No. 3, and the Hybrid Capture Method Various cervical smears were investigated for the presence of HPV using the Hybrid Capture II HPV DNA Test supplied by Digene Corporation, Gaithersburg, Md., USA; this test indicated that 15 samples were high-risk HPV-positive while 24 were high-risk HPV-negative.

These samples were also examined for HPV using the primer pair SEQ ID No. 1 and SEQ ID No. 3 and the PCR reaction shown in Example 2. In parallel, these samples were also examined using the GP5+/GP6+ primer pair and the reaction conditions specified in the Jacobs et al. publication, loc. cit.

While eleven out of the 15 HCII high-risk HPV-positive samples were positive with GP5+/GP6+, all 15 of the samples were positive with SEQ ID No. 1/SEQ ID No. 3.

Of the 24 HCII high-risk HPV-negative samples, a further two samples were positive with GP5+/GP6+ while as many as seven samples were positive with SEQ ID No. 1/SEQ ID No. 3.

In all the cases apart from one in which a positive finding was made using SEQ ID No. 1/SEQ ID No. 3, it was possible to identify the HPV type which was present by directly sequencing the amplificates. In the case of the total of 13 samples which were positive using GP5+/GP6+, it was only possible to do this in seven cases since patient samples were found to give rise to multiple bands in the gel, something which appeared to point to nonspecific amplificates of cellular genes. In two out of these seven cases the result differed from that which was obtained using SEQ ID No. 1/SEQ ID No. 3.

The HPV types which were found in this experiment using SEQ ID No. 1/SEQ ID No. 3 were: 2a, 16, 18, 31, 32, 33, 35, 42, 45, 51, 53 and 72.

These comparative experiments demonstrate that the primer pair SEQ ID No. 1/SEQ ID No. 3 is markedly more sensitive than the hybrid capture method or a method which uses the GP5+/GP6+ probes. In comparison to SEQ ID No. 1/SEQ ID No. 3, GP5+/GP6+ showed nine falsely negative samples whereas when compared with SEQ ID No. 1/SEQ ID No. 3, the hybrid capture method showed seven falsely negative samples.

What is claimed is:

1. A method for detecting human papillomaviruses (HPV) in biological material, comprising the steps of:
   (a) extracting and isolating nucleic acids from biological material, and
   (b) detecting HPV-specific DNA in the isolated nucleic acids, by detecting specific HPV DNA segments using a pair of oligonucleotides selected from the group consisting of the pair SEQ ID NO: 1 and SEQ ID NO: 2, or the complement thereof or the pair SEQ ID NO: 1 and SEQ ID NO: 3 or the complement thereof.

2. The method of claim 1, wherein the detection is effected by way of amplifying the specific HPV-DNA segments by means of a polymerase chain reaction (PCR).

3. The method of claim 2, wherein the PCR is characterized by the following temperature profile:

| | |
|---|---|
| Heating: | 5–15 min., 90–100° C.; |
| Heat denaturation: | 30–90 sec., 90–100° C.; |
| Hybridization: | 30–90 sec., 50–60° C.; |
| Polymerization: | 30–180 sec., 67–77° C.; |
| Cooling: | 2–10 min., 67–77° C. |

4. The method of claim 2, wherein the primer pair employed for the PCR comprises a pair of oligonucleotides consisting of SEQ ID NO: 1 and SEQ ID NO: 2.

5. The method of claim 3, wherein the primer pair employed for the PCR comprises a pair of oligonucleotides consisting of SEQ ID NO: 1 and SEQ ID NO: 2.

6. The method of claim 2, wherein the primer pair employed for the PCR comprises a pair of oligonucleotides consisting of SEQ ID NO: 1 and SEQ ID NO: 3.

7. The method of claim 3, wherein the primer pair employed for the PCR comprises a pair of oligonucleotides consisting of SEQ ID NO: 1 and SEQ ID NO: 3.

8. The method of claim 1, wherein the HPVs are typed by sequencing the detected HPV DNA segments.

9. The method of claim 2, wherein the HPVs are typed by sequencing the amplified HPV DNA segments.

10. The method of claim 3, wherein the HPVs are typed by sequencing amplified HPV DNA segments.

* * * * *

SEQUENCE LISTING

<160> NUMBER OF SEQ ID NOS: 3

<210> SEQ ID NO 1
<211> LENGTH: 27
<212> TYPE: DNA
<213> ORGANISM: Artificial Sequence
<220> FEATURE:
<223> OTHER INFORMATION: forward primer

<400> SEQUENCE: 1
aacaatgtgt agacattata aacgagc                                  27

<210> SEQ ID NO 2
<211> LENGTH: 23
<212> TYPE: DNA
<213> ORGANISM: Artificial Sequence
<220> FEATURE:
<223> OTHER INFORMATION: backward primer

<400> SEQUENCE: 2

```
attaaactca ttccaaaata tga                                         23
```

<210> SEQ ID NO 3
<211> LENGTH: 22
<212> TYPE: DNA
<213> ORGANISM: Artificial Sequence
<220> FEATURE:
<223> OTHER INFORMATION: backward primer

<400> SEQUENCE: 3

```
gaggytgcaa ccaaaamtgr ct                                          22
```